United States Patent [19]
Mitchell et al.

[11] Patent Number: 6,077,811
[45] Date of Patent: *Jun. 20, 2000

[54] VANADIUM COMPOSITIONS TO ENHANCE PLANT GROWTH AND EDIBLE FRUIT YIELD

[76] Inventors: James P. Mitchell, Box 517, Wolfforth, Tex. 79382; A. Wayne Wyatt, 3246 91st St.; James C. Conkwright, 9102 Vicksburg Ave., both of Lubbock, Tex. 79423; Charles W. Wendt, 4518 22nd St., Lubbock, Tex. 79407; Stan Hicks, 708 13th St., Shallowater, Tex. 79363

[*] Notice: This patent is subject to a terminal disclaimer.

[21] Appl. No.: 08/918,285

[22] Filed: Aug. 25, 1997

Related U.S. Application Data

[63] Continuation-in-part of application No. 08/467,018, Jun. 6, 1995, Pat. No. 5,661,105.

[51] Int. Cl.[7] ................................................... A01N 55/02
[52] U.S. Cl. ............................................................ 504/192
[58] Field of Search ............................................... 504/192

[56] References Cited

U.S. PATENT DOCUMENTS 5,186,738  2/1993  Wendt et al. .......................... 504/192
5,661,105  8/1997  Mitchell et al. ....................... 504/192

FOREIGN PATENT DOCUMENTS 334539   9/1989  European Pat. Off. .
608009   7/1994  European Pat. Off. .
1452237  7/1965  France .
8904371  5/1989  WIPO .

OTHER PUBLICATIONS

Walters et al., Rosidae, Vascular Plant Taxonomy, 3rd ed., 173–177, 1977.

Primary Examiner—Jose' G. Dees
Assistant Examiner—Alton Pryor
Attorney, Agent, or Firm—Henry Craskell

[57] ABSTRACT

A method for enhancing the growth of plants, flowering plants, fruits and vegetables produced by such plants through contacting the plants during growth periods with effective amounts of vanadyl compositions. These methods include compositions's application rates, time of application and other plant conditions such as stress, moisture levels and other growth variables in order to achieve enhanced fruit yields.

11 Claims, No Drawings

VANADIUM COMPOSITIONS TO ENHANCE PLANT GROWTH AND EDIBLE FRUIT YIELD

This application is a continuation-in-part of patent application Ser. No. 08/467,018 entitled "VANADIUM COMPOSITIONS TO ENHANCE PLANT GROWTH AND EDIBLE FRUIT YIELD" filed Jun. 6, 1995, now U.S. Pat. No. 5,661,105.

BACKGROUND OF THE INVENTION

This invention relates to methods of promoting the growth of plants and in particular it relates to methods for increasing the yield of fruit production of plants. In another aspect, the invention relates to increasing the rate of growth of legumes and yields of edible reproduction fruits of said legumes. In still another aspect, the application of effective amounts of the vanadyl compositions applied to plants during growth cycles has been found to promote plant growth and plant fruit yield in peanuts, a legume. In yet another aspect, the invention relates to increase quantity and quality of yields of flowering plants, vegetables and plant growth. Worldwide increasing population increases demands on horticulture efficiency and agricultural crop yields from all sources. The need to improve these efficiencies and yields is ever present especially in view of the loss of productive farm land. Thus, improved plant growth and plant fruit yields and quality are needed along with better utilization of agricultural lands in order to meet the increasing population growth food requirements. Plant growth regulators which can economize the use of fertilizers, nutrients, enzymes, and other growth promoters for various plants are being investigated continuously. Unfortunately, plant growth regulators and specific species of plants along with different generic classes of plants provides the researcher with less than predictable results even when utilizing same or similar compounds successfully applied to other species and generic classes.

Plant growth regulators can be defined as compounds and preparation which in minute amounts alter the behavior of crop plants or the produce of such plants through physiological (hormonal) tendencies rather than physical action. Plant growth regulators may either accelerate or retard growth, prolong or break a dormant condition, promoting rooting, fruit-set, or increase fruit size or quantity, or effect a growth and or productivity of plants in other ways. Plant growth regulation activity can vary from plant to plant as well as from novel composition to novel composition and specific combinations of the compositions and plants.

Various compositions have been studied as micro nutrients and plant growth promoters to increase crop productivity across a wide range of horticulture and agricultural crops. Compositions which include vanadium compounds have been studied and have results both beneficial and detrimental in effect on plants. Vanadium occurs in higher plants at levels usually between 0.2 and 4 ppm. Studies indicate that vanadium may have some effect on plants, including higher order plants which are of agricultural interest. Whether that effect is beneficial or detrimental appears to depend on the form of the vanadium, the type of plant and the method and timing of the application.

The importance of many metallic elements as integral constituents of enzymes and electron carriers warrants the attention of many plant physiologists. Aside from their roles as cofactors, activators are regulators in many enzymes' reactions, trace elements are essential to the maintenance of many biochemical processes in plants. Vanadium is one of the trace elements that is widely distributed in plants. Despite the fact that has been shown that vanadium increases growth in lettuce, tomatoes, asparagus, corn, barley and rice and the like, there is still no conclusive evidence that it is an essential element for higher plants. It does not meet the criteria of essentiality to the plant. However, vanadium on the other hand appears to be essential for many microorganisms. Continuing studies are being undertaken presently as they have in the past to investigate the distribution of vanadium and its effects on growth of agriculturally useful plants. Vanadium has stimulated growth and mazed plants at levels of 0.25 ppm in nutrient solutions. However, vanadium had no effect on lettuce or tomato plants at levels of 0.05 ppm. Lauchili et al. 15B ENCYCLOPEDIA OF PLANT PHYSIOLOGY 723–26 (1983). A study of the effect of a foliar spray of a vanadyl sulfate solution on leaf growth of sugar beet plants indicated that it decreased leaf growth, but that it increased the amount of reducing sugar in the roots of the sugar beet. Singh et al. 44 PLANT PHYSIOLOGY 1321–27 (1969). The use of vanadium (in the form of vanadyl lactate at concentrations of $10^{-3}$ to $10^{-6}$ molar) as a fertilizer has produced an increase in foliage yield of some higher plants. Kerr et al. Monograph 11 BRITISH PLANT GROWTH REGULATOR GROUP 103–21 (1984).

More recently vanadyl composition have been used in promoting the lint yield of fiber producing plants such as cotton by heating the plant during growth periods of the plant with an amount of a vanadyl salt of a carboxycilic acid. These compositions are found in U.S. Pat. No. 5, 186,738 hereby incorporated by reference; however the '738 patent reports that the vanadyl composition proved ineffective for promoting the growth of soybeans, a legume. Again illustrating the variations of experience with vanadyl compositiions in achieving regulation activity ie. plant growth and plant fruit growth enhancement from plant to plant. Thus, a continuing need exists for development of effective vanadium composition methods, timing and conditions of application in order to achieve enchanced edible fruit production.

SUMMARY OF THE INVENTION

The invention provides novel methods for enhancing the growth of plants, flowers, fruits and vegetables produced by such plants through contacting the plants during growth periods with effective amounts of vanadyl compositions. The invention also includes effective methods for applying the vanadyl compositions to plants to promote growth and fruit yields. These methods include composition's application rates, time of application and other plant conditions such as stress, moisture levels and the like in order to achieve enhanced fruit yields. The vanadium compositions specifically vanadyl ions have been effective on the plant growth, particularly plant fruit growth such as the edible fruits of legumes. Preferably, the vanadium compositions which are applied to the plants, influence the plants as vanadyl ions and one source of such compositions is the vanadyl salt of a carboxylic acid such as vanadyl lactae or vanadyl citrate. The plant may be treated by supplying the plant measured amounts of vanadyl compositions to the foliage of the plant or to the roots of the plant or a combination of both. Applying the roots of the plant is accomplished by applying the compositions to earth around the plant or irrigating the roots of the plant with the application in combination of water. In addition, the applications can be, by applying dry composition powder to the foliage of the plant which followed by rain, irrigation and the like, assist the plant in absorbing the vanadyl composition ions. Using one or more of these methods, the application of the composition is applied at least once during growth periods of the plant. Generally, the application of the composition is applied only once during the growth period of the plant preferably under moist conditions. The compositions are applied to achieve a treatment rate ranging from about 0.025 lbs per acre to about 0.1 to 0.2 lbs per acre of growing plants. In the case of peanuts, the application of 0.05 lbs per acre at the peg stage of growth increased peanut yields of at least about 5 percent by weight.

For fruit bearing plants including fruit bearing legumes, the application of the composition is applied to the plant from about 21 days before the start of the reproductive cycle of the plant to about 21 days after the start of the reproductive cycle of the plant. The start of the reproductive cycle of the plant is indicated by settling of blooms or similar states depending on the type of plant.

In one embodiment, the application form of the composition is an aqueous solution or emulsion which contains an effective concentration of vanadyl ions. The solution is prepared by dissolving, for example, an organic compound or a complex of vanadium in water which provides a source of vanadyl ions. The solution is then sprayed onto the foliage or leaf surfaces of the plants during the growth period of the plants and under preferably moist conditions.

The application form on the composition can be in solid, particular or powder form which includes an organic compound or complex of vanadium and is applicable to the earth around the plant. The solid composition particulate materials are applied by spreading around the plants during the growth period. The action of irrigation water or rain then causes the solid particles to dissolve and generates a solution which has an effective concentration of vanadyl ions. The aqueous solution flows into the ground around the roots of the plant and irrigates the roots of the plant.

The compositions of the invention and methods of applications of applying these compositions are particularly useful for promoting the growth of plant produced fruits. Specifically edible reproductive fruits of plants ie. legumes which are valuable and necessary food as well as other potential agronomic crops which may be shown to be influenced in plant growth enhancement and fruit yield.

In other embodiments, the invention provides novel methods for enhancing quantity and quality of yields of flowering plants, vegetables and plant growth. Vegetables are commonly defined as herbaceous plants such as cabbages, potatoes, beans, turnips and the like which are cultivated for an edible part used as a table vegetable. An edible part of the plant such as seeds, leaves, roots, bulbs and the like are contrasted with fruits. However, tomatoes are botanically considered to be a fruit therefore the term fruit or vegetable for the purposes of this invention disclosure are defined as those plant produced edible portions whether vegetable or fruit. In addition, the present invention relates to the enhancement of plant foliage, leaves and the like as well as quality and quantity of flowers produced by flowering plants. Generally, a plant is defined as a young tree, vine, shrub or herb planted or suitable for planting and can be comprised of vegetables, flowers, fruits or ornamental plants grown for landscaping and the like.

DETAILED DESCRIPTION OF THE INVENTION

The invention provides a method for increasing the rate of growth of plants, flowers and yields of flower and/or edible reproductive fruit of said plants achieved by supplying to the plants which produce edible reproductive fruits on at least one occasion during growth cycles of the plant, an effective amount of vanadyl ions. The method of this invention can be employed to increase vegetative growth and to increase fruit production of fruit producing plants. The vanadium composition used in the methods of this invention have broad spectrum plant growth regulation capacity that can be employed to stimulate the growth and/or fruit-producing capability of plant varieties, including fruiting and princibly vegetative plants. Fruiting plants, for the purpose of the invention include plants that bear any variety of produce other than vegetative growth such as annual or perennial vegetables, fruits, nuts and the like. Varieties of vegetables which can be treated in accordance with the methods of the invention include bulb plants such as onions, tuberous crops such as potatoes, sugar beets and peanuts (legumes), beans, peas and the like. Treatable nut crops include walnuts, pecans, almonds, cashews and the like can also be enhanced.

Vanadium is a transition metal which displays well-characterized valence states of +2 through +5 in solid compounds and in solution. Vanadium easily forms oxycations such as vanadyl ions $(VO)^{2+}$ which are composed of vanadium metal and oxygen. The valence state of vanadium in a vanadyl ion is +4. Many compounds or complexes which include vanadium may be used to generate the vanadyl ions.

For example, vanadium forms compounds or complexes with various organic compounds such as carboxylic acids. Carboxylic acids are characterized as organic compounds that contain at least one carboxyl group. The carboxyl group is represented chemically as:

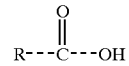

where R is a saturated or unsaturated organic group which includes one or more carbons.

Formic, acetic, propionic, and butyric acid are examples of carboxylic acids which contain one carboxyl group and form compounds or complexes with vanadyl ions. Likewise, oxalic, malonic, succinic, glutaric, adipic, maleic, and fumaric acid are examples pf dicarboxylic acids which contain two carboxyl groups and form compounds or complexes with vanadyl ions. Further, other carboxylic acids with one or more carboxyl groups such as glycolic, lactic. glyceric, citric, tartaric, and malic acid form compounds or complexes with vanadyl ions. Organic compounds or complexes of vanadyl ions may also occur in polymeric form. The term "carboxylic acid" as used herein means any organic compound which includes one or more carboxyl groups, and specifically includes the compounds noted above.

Other compounds or complexes which contain vanadyl ions may also be used in the compositions of the invention. For example, a diketone such as acetylacetone forms vanadyl acetylacetonate which may be used in the compositions of the invention.

Some vanadium compounds are ineffective for promotion of plant growth, especially plant fruit growth. For example, vanadate compounds which generate the vanadate ion $(VO_2)+$ in which vanadium has a +5 valence state have been found to be detrimental to plant growth.

The compositions of the invention may be prepared in concentrate form or application form. For example, the composition may be made in solid particulate form which may be bagged and easily transported to a desired plant crop location. At the plant crop location the solid form may be mixed with water to create a solution which may be sprayed onto the foliage of plants. The solid particulate form of the composition may include an organic compound or complex of vanadium which may generate vanadyl ions when dissolved in the water. The solid particulate form would also include a conventional agricultural carrier agent in solid form.

Conventional liquid agricultural carrier agents may also be used in the various forms of the composition. Generally, the organic compound or complex of the vanadyl ions will be dissolved or dispersed in the liquid carrier agent. Preferably, water is used as the liquid carrier agent. Other conventional agricultural oils may also be used as the liquid carrier agent. For example, a liquid concentrate form of the composition may be prepared by dissolving or dispersing an amount of an organic compound or complex of vanadyl ions in water. The liquid concentrate is then containerized and transported to a plant crop location and mixed with more water to prepare an application form of the composition with an effective concentration of the vanadyl ions in solution. The application form of the composition is then sprayed onto the foliage of the plants.

Generally, the vanadyl ion compositions of the invention has potential for application to any type of plant to promote growth. The term "promote growth" means improving the number, size, quantity, or quality of fruits that grow on the plants. The term "promote growth" also encompasses characterizations of the effect of the composition on plants such as yield enhancer, fertilizer, and micro-nutrient. Plant fruit in this context includes any seed bearing organ of a plant such as beans, tublers, bulbs, peas and the like. The vanadyl ion compositions additionally improve the water and nutrients use efficiency of plants as one aspect of promoting the growth of the plants.

Other ingredients may be added to the composition to produce specific effects. For example, adhesives, thickeners, penetrating agents, spray oils, stabilizers, preservatives, surfactive agents, fertilizers, micronutrients, pesticides may be added to the composition as desired.

The vanadyl ion composition is applied to the plant during the growth period of the plant. The time and number of applications of the composition are dependent upon the type of the plant and the desired effect. For example, to promote fruit growth, the composition should be applied during the time period from shortly before the start of the reproductive stage of the plant to shortly after the start of the reproductive stage of the plant. The start of the reproductive stage of the plant is characterized by the setting of blooms, or a similar stage indicating the beginning of the fruit depending on the type of plant.

Preferably, the vanadyl ion composition is applied between about 21 days before the start of the reproductive stage of the plant to about 21 days after the start of the reproductive sage of the plant. For cotton, the preferred application time period is from 14 days prior to the setting of blooms to 7 days after the setting of the blooms. For any particular plant the optimal time for applying the vanadyl ion composition within the period of 21 days before to 21 days after the start of the reproductive stage may be determined using conventional techniques.

Different methods may be used to apply the vanadyl ion compositions to plants. For example, a liquid form of the composition may be applied to the leaves or foliage of plants. This may be accomplished using conventional agricultural spray devices. Both liquid and solid forms of the composition may be applied to earth surrounding plants. For example, conventional watering systems may be used to apply a liquid form of the composition to earth around plants. Further, the composition may be applied to the roots of the plants. For example, the liquid form of the composition may be injected into the ground around the roots of the plants by using underground pipes or hoses.

To maintain the vanadyl ions in the liquid form of the composition, it is necessary to control the pH of the composition. Otherwise the vanadyl ions might be converted to other noneffective vanadium ions such as vanadate ions. Generally, the application form of the composition should be maintained at a pH ranging from about 4 to 9 to maintain the vanadyl ions. Preferably, the pH is maintained in the range of about 6 to 8. Depending on the ingredients in the composition, the pH may be controlled by adding a buffering agent.

The following examples were based on the application of 0.05 lbs of vanadium compound per acre to peanuts at the peg stage of growth and are compared to control plots in the same field.

EXAMPLE 1

Vanadyl composition were applied to peanut plants at the peg stage of growth under moist conditions in a 20 acre plot of a total 60 acre field of peanuts. The entire 60 acres of peanuts being planted, cultivated, fertilized and irrigated under exactly the same conditions which allowed for direct comparisons of the yields of the treated peanuts ie. 20 acres versus the control 40 acres. The treated acreage of 20 acres of peanuts provided a yield of 5,197.30 lbs per acre while the control acreage (40 acres) yielded 4,815.35 lbs per acre. The vanadium treated peanuts produced a 7.9 percent increase in peanuts ie. fruit yield. Application date was on August 3 at 8 am and was delivered by air means under moist conditions, plant moist conditions ie. moist foliage conditions.

EXAMPLE 2

A 120 acre field of peanuts was divided into a 20 acre plot wherein vanadyl composition applications were made to the peanuts versus a control of 100 acres of peanuts. The entire 120 acres of peanuts being planted, cultivated, fertilized and irrigated under the same conditions which allowed for direct comparisons of the yields of the peanuts ie. 20 acres versus the control 100 acres. The treated peanuts yield 3,518.20 lbs per acre (20 acre plot) and the control peanuts (100 acres) yielded 3,117.16 lbs per acre. The application date was Aug. 3, 1993 at 8:10 am by air means when the peanut plants foliage was in a moist condition.

Overall the test plots were visually impressive. A visual difference existed between the treated and untreated plants. The treated peanuts had a darker green color and seemed to be in a more healthy growth mode. The peanuts at harvest time on the vanadium treated plants were positioned in a tight ball around the roots instead of being more scattered out on the vine. The pods also seemed to be more completely filled. The treated peanuts looked more mature. However, this observation was not reflected in the grade.

In Example 2, the greatest difference in appearance and yield was observed. The peanuts went through a great deal of stress mainly yellow herbicide damage as compared to the peanuts of Example 1. The treated vines were not as stunted at harvest as the untreated. The USDA grade sheets, however, produced no differences in grade between the treated and the untreated. From the results, vanadium compositions and the respective applications of these compositions is very desirable as to the yields of produced fruit (peanuts) and are most cost effective for the increased yields.

The application of vanadium compounds to other crops frequently fails to show significant results from the treatments. Most of these crops tested have been during unusual weather years, causing poor crop stands that give mixed results. The effectiveness of vanadium composition treatment on enhanced growth and plant fruit yields of other crops is still to be determined based on application rates and conditions of applications. What here before has been reported as inconclusive or negative results may, with additional exploration of conditions, application rates and timing of applications, produce similar improved results with vegetable such as onions, potatoes, carrots, beans, peas and the like.

Useful vanadyl compositions can be prepared by four to five multiration of lactic acid added to a solution of vanadium pentoxide in a working volume of water. The working volume of water will be dependent upon the amount needed to prepare the overall solution. The mixture of lactic acid, vanadium pentoxide and water is stirred and heated as a result that the vanadium pentoxide and lactic acid react to farm vanadyl lactate in its ionic form which includes vanadyl ions. The vanadyl ions will be characterized by dark blue color in the solution. The pH of the solution will be acidic due to the lactic acid and the pH should be adjusted to approximately neutral for dilution and addition to respective plant foliage or at root systems.

EXAMPLE 3

A vanadial salt of a carboxylic acid composition was applied to various fern plants, potted in 3 gallon pots, the fern plants were large plants having been in the pots for 1 year. The fern plants, as treated, exhibited deeper green color and vigorous growth as compared to control plants of the same age and size which were maintained under identical conditions but without treatment. The vanadium composition treated plants which were foliage contacted with the equivalent vanadium composition ranging from about 0.025 lbs per acre to about 0.1 to about 0.2 lbs per acre of growing fern plants.

Several control plants and several treated plants were placed in direct exposure to west Texas, August environment; the control plants died in 15 days without any added water while the treated plants without added water lost substantial portions of the leaf area but recovered to a good condition with added water in about 10 days.

EXAMPLE 4

Vanadium compositions were applied to three healthy and vigorous rose plants, Three untreated control rose plants of the same age, size and general condition were maintained under the same conditions with the vanadium composition treated rose plants producing deeper green leaf, size of leaf with larger and firmer blooms as compared to the control plants. A treatment was applied during budding of the plants in the spring and a second vanadium composition treatment was applied to the treated plants ie. the three rose plants in July with continuing enhancement of leaf, green intensity of color, size and bloom size as well as quality of bloom. The six rose plants, three control and three treated, were observed for two years and on the third year the control plants were treated and the previously treated plants were not treated with the result that the previously control plants produced deeper green and larger sized leafs as well as better quality blooms as compared to the previously treated plants which during the year were not treated with vanadium compositions. The vanadium composition was the vanadial composition of carboxylic acid and was applied at the same rate as indicated in Example 3.

EXAMPLE 5

Several verbenas were treated with the vanadial compositions of Example 3 in the proportion amounts as indicated in Example 3 with the result of vigorous blooming plants and flowering qualities. No controls were maintained, however, observations showed that the treated verbenas were noticeably improved as compared to previous years.

EXAMPLE 6

Various chrysanthemum plants were also treated in accordance with the procedures of Example 3 with vigorous growth results inclusive of deeper green leaves and plants as well as quantity and quality enhancement of the mums produced. No control plants were utilized in this study, however, observations of the quality of the chrysanthemums versus prior experience was that the vanadial composition treated chrysanthemums produced hardier and more vigorous plants and flowers. As compared to prior experience within the same planting environment.

EXAMPLE 7

Three varieties of tomato plants inclusive of cherry tomatoes, early grown tomatoes and patio tomatoes were studied with treated plants of all three varieties, treated in accordance with the procedure of example 3 and compared to control plants of the three varieties which were not treated with vanadial compositions The results showed the following contrast; the treated plants had larger stems, earlier fruit production and more fruit ie. more tomatoes as compared to the control or non treated plants. The increased production of fruit yields were from about 10–30% enhancement in the treated plants.

EXAMPLE 8

Irish potato plants control and treated plants were studied wherein the treated plants were treated in accordance with Example 3 and the control plants received no vanadial composition treatment. The potato plants both control and treated, received the same amount of irrigation water in the same field under the same environmental conditions with the treated plants producing more number 1 or more giant potatoes as compared to the control or untreated plants. The control plants produced smaller potatoes while the treated plants produced more giant or large potatoes but still produced as many or more potatoes in total than the control.

EXAMPLE 9

Geraniums were cultivated utilizing ten treated and ten controlled plants, the treated plants being treated in accordance with the vanadial composition applications of Example 3. The treated geraniums ie. treated with vanadial compositions, produced deeper color foliage, deeper colors and enhanced blooms, the blooms staying on the plants longer and of larger size as compared to the control. There were 20 plants that were treated and 20 control plants with a difference noted between the control and treated plants as early as 3–5 days after vanadyal composition foliage applications.

The examples and embodiments described above illustrate the invention and changes in modifications can be made without departing from the scope of the invention. It is intended that such changes modifications fall within the scope of the invention as defined by the appended claims.

What is claimed is:

1. A method for increasing the rate of growth of plants and yields of edible reproductive fruits of said plants comprising;

supplying to the plants which produce edible reproductive fruits on at least one occasion during growth cycles of the plants in effective amount of vanadium compositions consisting essentially of a vanadyal salt of carbocyclic acid from promoting the yield of edible reproductive, fruit consisting of the tomato.

2. A method for increasing the rate of growth of plants and yields of edible reproductive vegetables of said plants, comprising;

supplying to the plants which produce edible reproductive vegetables on at least one occasion during growth cycles of the plants and effective amount of vanadyal composition consisting essentially of vanadyal salt of a carboxylic acid for promoting the yield of edible reproducible vegetables, wherein the edible productive vegetables are selected from the groups consisting of tubulars and bulbs.

3. The method according to claim 2 wherein the edible reproductive vegetable is a potato.

4. The method according to claim 2 wherein the edible reproductive vegetable is a sweet potato.

5. The method according to claim 2 wherein the edible reproductive vegetable is an onion.

6. The method to claim 2 wherein the plant is treated with the composition at a rate ranging from about 0.025 lbs per acre to about 0.1 to about 0.2 lbs per acre of growing plants.

7. A method for increasing the rate of growth of plants, comprising;

supplying to the plants on at least one occasion during growth cycles of the plants and effective amount of vanadyal composition consisting essentially of vanadyal salt of a carboxylic acid for promoting quality and quantity of the plant foliage, and the plant as a fern.

8. A method for increasing the rate of growth of flowering plants and yields of flowers other flowering plants comprising;

supplying to the flowering plants which produce decorative flowers on at least one occasion during growth cycles of the plants and effective amount of a vanadyal composition consisting essentially of a vanadyal salt of a carboxylic acid from promoting the yields of the flowers of the flowering plants wherein the flowering plants are comprised of roses.

9. A method for increasing the rate of growth of flowering plants and yields of flowers other flowering plants comprising;

supplying to the flowering plants which produce decorative flowers on at least one occasion during growth cycles of the plants and effective amount of a vanadyal composition consisting essentially of a vanadyal salt of a carboxylic acid from promoting the yields of the flowers of the flowering plants wherein the flowering plants are comprised of verbenas.

10. A method for increasing the rate of growth of flowering plants and yields of flowers other flowering plants comprising;

supplying to the flowering plants which produce decorative flowers on at least one occasion during growth cycles of the plants and effective amount of a vanadyal composition consisting essentially of a vanadyal salt of a carboxylic acid from promoting the yields of the flowers of the flowering plants wherein the flowering plants are comprised of geraniums.

11. A method for increasing the rate of growth of flowering plants and yields of flowers other flowering plants comprising;

supplying to the flowering plants which produce decorative flowers on at least one occasion during growth cycles of the plants and effective amount of a vanadyal composition consisting essentially of a vanadyal salt of a carboxylic acid from promoting the yields of the flowers of the flowering plants wherein the flowering plants are comprised of chrysanthemums.

* * * * *